(12) United States Patent
Benn

(10) Patent No.: US 10,376,303 B2
(45) Date of Patent: Aug. 13, 2019

(54) ELECTROSURGICAL ELECTRODE AND INSTRUMENT

(71) Applicant: GYRUS MEDICAL LIMITED, Cardiff (GB)

(72) Inventor: Christopher Charles Benn, Bristol (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 744 days.

(21) Appl. No.: 14/515,239

(22) Filed: Oct. 15, 2014

(65) Prior Publication Data
US 2015/0105777 A1    Apr. 16, 2015

(30) Foreign Application Priority Data
Oct. 15, 2013    (GB) .................................. 1318204.3

(51) Int. Cl.
*A61B 18/14*    (2006.01)
*A61B 18/00*    (2006.01)

(52) U.S. Cl.
CPC ........ *A61B 18/1402* (2013.01); *A61B 18/148* (2013.01); *A61B 18/1482* (2013.01); *A61B 2018/00601* (2013.01); *A61B 2018/00607* (2013.01); *A61B 2018/00625* (2013.01); *A61B 2018/142* (2013.01); *A61B 2018/1412* (2013.01); *A61B 2018/1422* (2013.01); *A61B 2218/007* (2013.01)

(58) Field of Classification Search
CPC ............ A61B 2018/1405; A61B 18/14; A61B 18/148; A61B 18/1485; A61B 2218/007; A61B 2218/008; A61B 2018/1422
See application file for complete search history.

(56) References Cited

U.S. PATENT DOCUMENTS 6,004,319 A    12/1999    Goble et al.
6,210,405 B1    4/2001    Goble et al.
(Continued)

FOREIGN PATENT DOCUMENTS

JP    2003-116870 A    4/2003
JP    2008-510530 A    4/2008
WO    WO 2009/146260 A1    12/2009

OTHER PUBLICATIONS

Mar. 13, 2015 extended Search Report issued in European Patent Application No. 14187678.9.
May 7, 2014 United Kingdom Search Report issued in United Kingdom Application No. GB1318204.3.
(Continued)

*Primary Examiner* — Jaymi E Della
(74) *Attorney, Agent, or Firm* — Oliff PLC

(57) ABSTRACT

An electrosurgical instrument is provided for the treatment of tissue, the instrument (3) comprising an instrument shaft (14) having a longitudinal axis, a suction lumen (16) extending at least partially along the instrument shaft, and a chisel electrode (21) at the distal end of the shaft. The chisel electrode (21) includes a body portion (22) at a first angle with respect to the longitudinal axis, and a hook portion (23) extending from the body portion at a second angle to the longitudinal axis. The chisel electrode (21) also includes a plurality of apertures (35, 36, 37, 38, 40) providing a suction lumen through the electrode, there being at least one aperture (35, 36, 37, 38, 42) in the body portion (22), and at least one aperture (40, 45) in the hook portion (23).

11 Claims, 4 Drawing Sheets

(56) References Cited

U.S. PATENT DOCUMENTS

| | | |
|---|---|---|
| 6,482,202 B1 | 11/2002 | Goble et al. |
| 6,832,998 B2 | 12/2004 | Goble |
| 2002/0103497 A1* | 8/2002 | Satou ............. A61B 17/320068 606/169 |
| 2003/0225403 A1* | 12/2003 | Woloszko ............ A61B 18/148 606/41 |
| 2005/0043728 A1 | 2/2005 | Ciarrocca |
| 2005/0107782 A1* | 5/2005 | Reschke ............ A61B 18/1402 606/42 |
| 2005/0273097 A1 | 12/2005 | Ryan |
| 2006/0293653 A1* | 12/2006 | Van Wyk ........... A61B 18/1485 606/41 |
| 2009/0069802 A1 | 3/2009 | Garito et al. |
| 2010/0023007 A1* | 1/2010 | Sartor .................. A61B 18/149 606/49 |
| 2010/0191173 A1* | 7/2010 | Kimura .......... A61B 17/320068 604/21 |
| 2010/0204690 A1 | 8/2010 | Bigley et al. |
| 2011/0054461 A1* | 3/2011 | Dickhans ............ A61B 18/148 606/33 |
| 2011/0196366 A1 | 8/2011 | Humble |
| 2011/0319887 A1* | 12/2011 | Keppel ................ A61B 18/042 606/41 |
| 2014/0343548 A1* | 11/2014 | Benn .................. A61B 18/1402 606/41 |

OTHER PUBLICATIONS

Apr. 24, 2018 Office Action issued in Japanese Patent Application No. 2014-209732.

\* cited by examiner

ELECTROSURGICAL ELECTRODE AND INSTRUMENT

TECHNICAL FIELD

This invention relates to an electrosurgical electrode and to an electrosurgical instrument for the treatment of tissue. Such instruments are commonly used for the vaporisation and/or coagulation of tissue in surgical intervention, most commonly in "keyhole" or minimally invasive surgery, but also in "open" surgery.

BACKGROUND TO THE INVENTION AND PRIOR ART

There is a frequent requirement during a surgical procedure for suction in order to remove matter from the surgical site, whether it is tissue debris, smoke, fluid, gas bubbles or other unwanted matter that interfere with the procedure or obscure the surgeon's view of the surgical site. U.S. Pat. Nos. 6,210,405 & 6,482,202 describe examples of this type of surgical instrument, and embodiments of the present invention provide an improvement to such suction instruments.

SUMMARY OF THE INVENTION

Accordingly, from one aspect a chisel electrode is provided for an electrosurgical instrument, the electrode having a longitudinal axis and comprising a body portion at a first angle with respect to the longitudinal axis, and a hook portion extending from the body portion at a second angle to the longitudinal axis, the electrode including a plurality of apertures providing a suction lumen through the electrode, there being at least one aperture in the body portion, and at least one aperture in the hook portion.

Prior art instruments with chisel electrodes provide suction by means of a suction tube terminating adjacent the chisel electrode. Embodiments of the present invention provide suction through a plurality of apertures present in the electrode itself, thereby directing the suction to the immediate area in which the tissue is being treated. In addition, the presence of the apertures within different portions of the electrode mean that it is much less likely that all of the apertures will be blocked at the same time, and hence suction should be maintained throughout use.

The electrode of the present invention includes a body portion and a hook portion. As there is at least one aperture in the body portion, and at least one aperture in the hook portion, this enables material to be aspirated from the vicinity of the electrode regardless of whether it is adjacent the body portion or the hook portion of the electrode. Typically, the first angle is non-zero, meaning that both the body portion and the hook portion extend at an angle to the longitudinal axis of the electrode. However, conceivably the first angle is zero, meaning that the body portion is aligned with the longitudinal axis of the electrode, and only the hook portion extends at an angle to the longitudinal axis.

According to one convenient arrangement, the body portion is circular in cross-section, typically tapered such that it forms part of a cone. Alternatively, the electrode also includes side faces on the body portion, the side faces facing laterally of the longitudinal axis. Where the electrode includes such side faces, there is preferably at least one aperture on each of the side faces. Conveniently, the electrode also includes one or more end faces at the distal tip of the electrode, typically part of the hook portion. Where the electrode includes such end faces, there is preferably at least one aperture in an end face of the electrode.

The body portion conveniently includes a prime suction lumen, and the plurality of apertures are in communication with the prime suction lumen. In this way, however many apertures are present, and however they are disposed with respect to the chisel electrode, they are all connected to a single suction lumen for the aspiration of material. Typically, the suction lumen is centrally located with respect to the body portion, running axially along the longitudinal axis of the electrode.

From another aspect embodiments of the invention further provide n electrode for an electrosurgical instrument, the electrode comprising a body portion having a suction lumen therein defining a longitudinal axis of the electrode, and a chisel-shaped hook portion extending from a distal end of the body portion at an angle to the longitudinal axis, a plurality of suction apertures being formed in the surface of the electrode and extending through the electrode to provide fluid connection to the suction lumen, the plurality of suction apertures being distributed across the surface of the electrode so as to face in different directions.

The distribution of the plurality of suction apertures across the surface of the electrode and the fact that the suction apertures face in different directions means that it is much less likely that all of the electrodes will be blocked at the same time either by the tissue being treated, or tissue debris, and hence suction should be maintained more easily throughout the surgical procedure.

In one embodiment at least one suction aperture is provided on the chisel shaped hook portion, and at least one suction aperture provided on the body portion. In most embodiments the suction aperture on the chisel shaped hook portion is forwardly facing i.e. faces generally in the axial direction of the electrode, whereas the suction aperture or apertures in the body portion face in different directions i.e. at angles from the axial direction. In some embodiments the suction aperture or apertures on the body portion face in a direction substantially orthogonal to the axial direction of the electrode defined by the suction lumen. In further embodiments there are a plurality of suction apertures provided on the body portion, substantially equiangularly arranged around the longitudinal axis facing outwards therefrom.

Embodiments of the invention further reside in an electrosurgical instrument comprising an instrument shaft having a longitudinal axis, a suction lumen extending at least partially along the instrument shaft, and a chisel electrode at one end of the shaft, the chisel electrode comprising a body portion at a first angle with respect to the longitudinal axis, and a hook portion extending from the body portion at a second angle to the longitudinal axis, the chisel electrode including a plurality of apertures in communication with the suction lumen, there being at least one aperture present in the body portion, and at least one aperture being present in the hook portion.

In a convenient arrangement, the instrument also includes a return electrode, and operates as a bipolar electrosurgical instrument. In a first arrangement, the electrosurgical instrument is such that it is designed to be operated in a conductive fluid, with the conductive fluid completing the current path between the electrodes. This means that the system operates to perform what is known as "underwater" electrosurgery, in which the conductive site is immersed in a conductive fluid such as saline, and the electrodes operate immersed in said conductive fluid. An example of this type of electrosurgical system is given in our earlier U.S. Pat. No. 6,004,319. The power and voltage settings used by a generator powering the instrument are such that the conductive fluid surrounding the electrodes is vaporised when the electrosurgical instrument is operated in its cutting mode. The provision of suction apertures, not only in the body portion of the electrode but also in the hook portion thereof, allows for fluid to be evacuated from the surgical site, helping to ensure that the fluid is replenished with a fresh supply of conductive fluid. Other debris, such as vaporised tissue particles, gas bubbles, and other matter can be evacuated from the surgical site through the apertures, to help maintain the visibility of the surgical site.

Alternatively, the electrosurgical instrument is such that it is designed to be operated in a dry-field environment, with the electrodes being in direct contact with the tissue to be treated, and with the tissue completing the current path therebetween. An example of this type of electrosurgical system is given in our earlier U.S. Pat. No. 6,832,998. The power and voltage settings used by the generator powering the instrument are generally lower than in underwater electrosurgical systems, as the electrodes contact the tissue directly and there is no need to form a pocket of vaporised saline surrounding the electrode. In this instance, the suction apertures are used for the evacuation of tissue particles or smoke particles, both of which can obscure the field of view if not removed from the surgical site.

DESCRIPTION OF THE DRAWINGS

Embodiments of the invention will now be further described, by way of example only, with reference to the accompanying drawings, in which.

DESCRIPTION OF THE EMBODIMENTS

Figure 1:
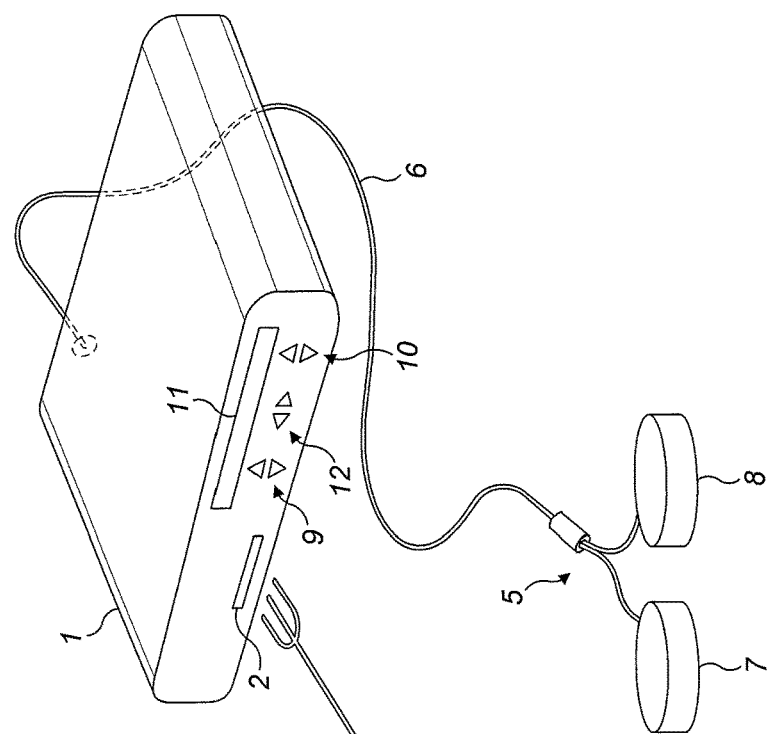
FIG. 1 is a schematic diagram of an electrosurgical system including an electrosurgical instrument in accordance with an embodiment the present invention.
Figure 1:
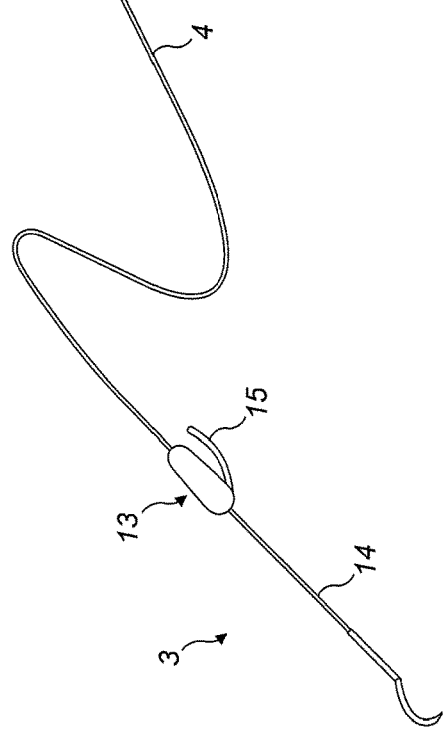
Figure 2:
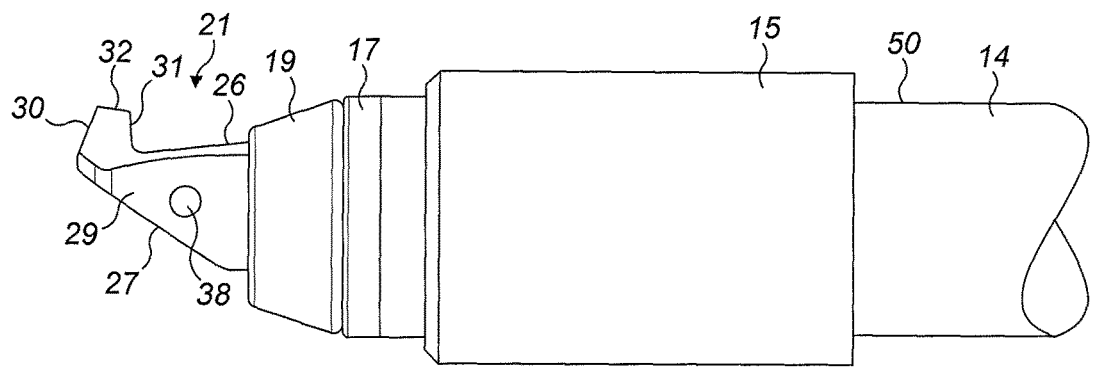
FIG. 2 is a side view of the tip of an electrosurgical instrument in accordance with the embodiment of the present invention used in the system of FIG. 1.
Figure 3:
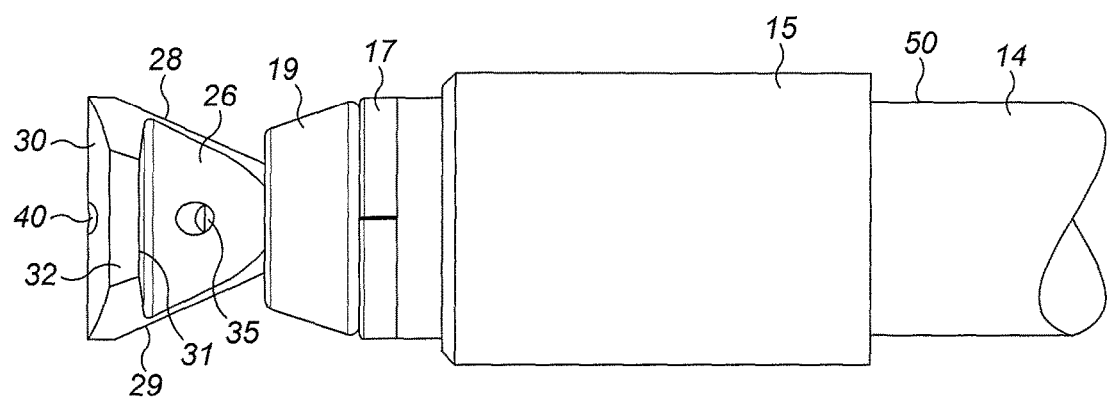
FIG. 3 is a plan view of the tip of FIG. 2.
Figure 4:
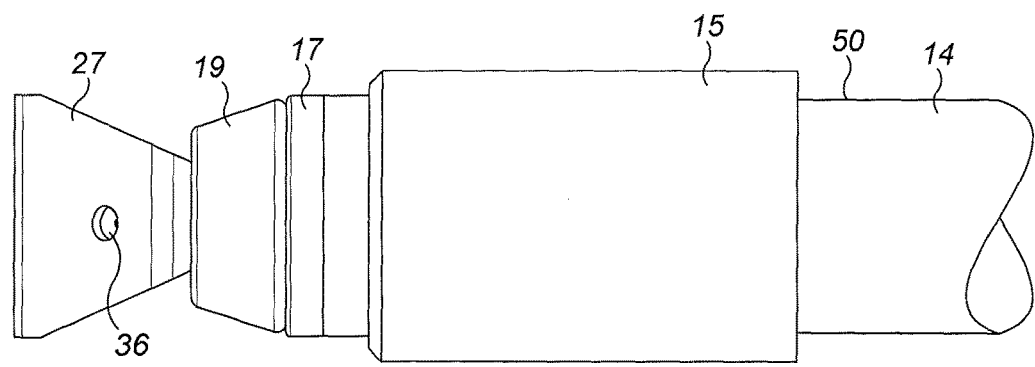
FIG. 4 is a underneath view of the tip of FIG. 2.
Figure 5:
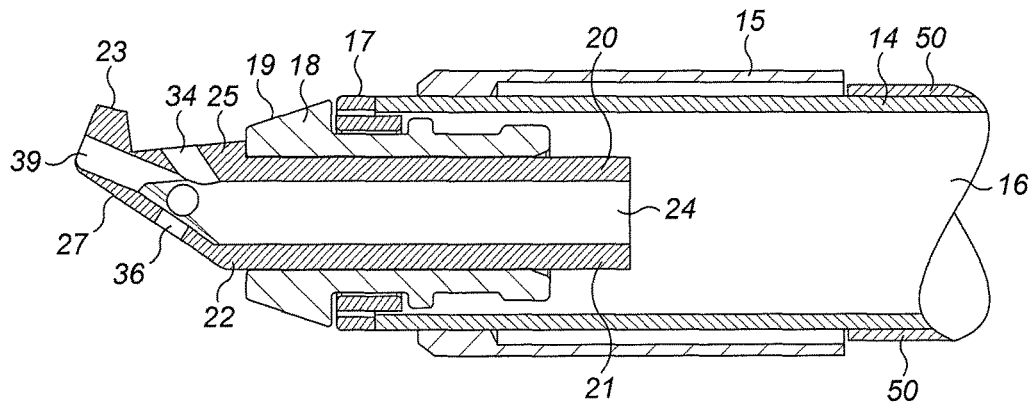
FIG. 5 is a sectional side view of the tip of FIG. 2.
Figure 6:
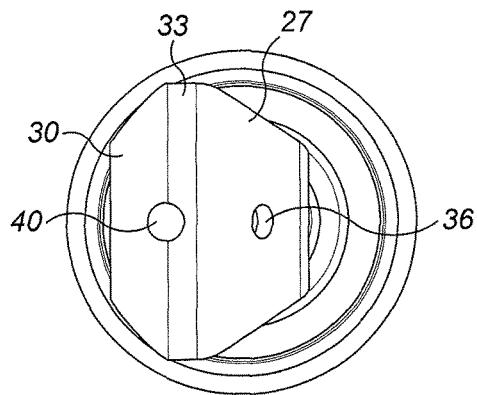
FIG. 6 is an end view of the tip of FIG. 2.
Figure 7:
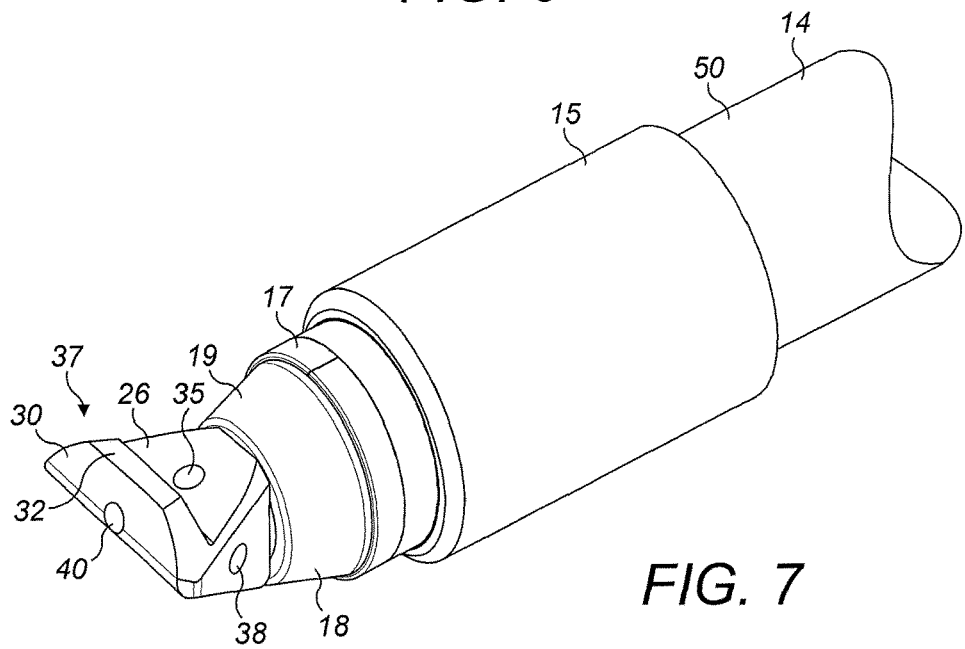
FIG. 7 is a perspective view of the tip of FIG. 2.

Referring to the drawings, FIG. 1 shows electrosurgical apparatus including a generator 1 having an output socket 2 providing a radio frequency (RF) output, via a connection cord 4, for an electrosurgical instrument 3. Activation of the generator 1 may be performed from the instrument 3 via a handswitch (not shown) on the instrument 3, or by means of a footswitch unit 5 connected separately to the rear of the generator 1 by a footswitch connection cord 6. In the illustrated embodiment, the footswitch unit 5 has two footswitches 7 and 8 for selecting a desiccation mode and a vaporisation mode of the generator 1 respectively. The generator front panel has push buttons 9 and 10 for respectively setting desiccation and vaporisation power levels, which are indicated in a display 11. Push buttons 12 are provided as an alternative means for selection between the desiccation and vaporisation modes.

The electrosurgical instrument 3 comprises a housing 13 with an elongate shaft 14, and tissue treatment electrodes at the distal end of the shaft, as will be described below. A movable handle 15 associated with the housing can be actuated to cause the shaft to bend. This instrument is particularly suited to the treatment of the hip joint, where a relatively long shaft with articulation capability is needed to access the area to the treated.

FIGS. 2 to 7 show the distal end of the shaft 14, which is provided with a metallic collar 15, acting as a return electrode. The shaft 14 is hollow, such that it defines an internal suction lumen 16, and the proximal part of the shaft 14 is covered with an insulating sheath 50. Located within the end of the shaft is an insulating collar 18, held in place by a metallic retaining ring 17. The collar 18 has a tapered front section as shown at 19, and has a central bore 20 into which is fitted a metallic electrode member 21. The electrode member 21 comprises an elongate body portion 22, and an upturned hook portion 23. The body portion 22 is hollow such that it forms a suction tube 24 which is in communication with the suction lumen 16 within the shaft. The body portion 22 also includes a stem section 25 extending from the insulating collar 18 and including a top face 26, bottom face 27, and side faces 28 & 29. The stem section 25 increases in width as it extends distally from the collar 18.

The hook portion 23 is located at the distal end of the stem section, and includes front and back faces 30 & 31 tapering towards a top edge 32. Between the front face 30 of the hook portion and the bottom face 27 of the body portion is an end face 33, constituting the distal-most part of the electrode member 21.

A bore 34 runs through the body portion 22 from the suction tube 24 to the top face 26 terminating in a suction aperture 35. Similar bores run from the suction tube 24 through the body portion 22 to the bottom face 27, and to the side faces 28 & 29, terminating in suction apertures 36, 37 & 38 respectively. Finally, a bore 39 runs from the suction tube 24 through the hook portion 23 to the end face 33, terminating in suction aperture 40. In all, there are five different suction apertures, each on a different face of the electrode member 21.

In use, the user manipulates the instrument 3 such that the electrode member 21 is adjacent tissue to be treated, and activates the generator 1 to supply RF power to the electrode member 21, via a lead (not shown). The hook portion 23 and the exposed parts of the body portion 22 act as the active electrode in a bipolar electrode arrangement, with the collar 18 acting as the return electrode. The suction lumen 16 is connected to a source of suction such that fluid, tissue fragments, bubbles or other debris in the vicinity of the electrode member 21 can be aspirated from the surgical site, via suction apertures 35, 36, 37, 38, & 40. The presence of the suction apertures in the different faces of the body portion 22, and in the hook portion 23, mean that whatever the orientation of the instrument, material can be aspirated from the surgical site regardless of its relative location with respect to the electrode member 21. The multiple suction apertures also allow for the suction effect to be maintained even if one aperture is temporarily blocked by a large tissue fragment or because that portion of the electrode member is embedded in the tissue to be treated. More generally, these advantageous effects are obtained due to presence of the multiple suction apertures located at different positions across the face of the instrument, and facing in different directions, such that they cannot all be occluded by tissue at the same time.

As previously mentioned, the instrument 3 is primarily designed to be operated in a conductive fluid such as saline, with the fluid completing the circuit between the electrodes. However, the instrument 3 can also be used as a dry-field instrument, in which case the user must ensure that the electrodes are placed in contact with the tissue to be treated. In this way, the current flows from the tissue treatment electrode, through the tissue, to the collar 18.

Figure 8:
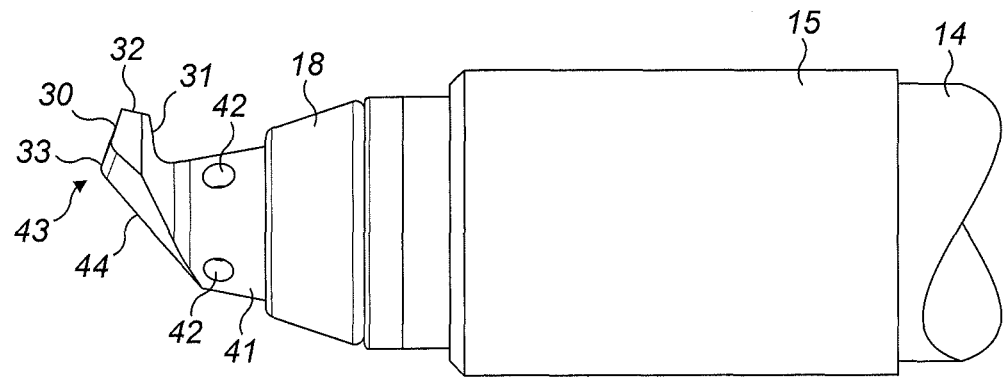
FIG. 8 is a side view of the tip of an alternative embodiment of electrosurgical instrument in accordance with the present invention.
Figure 9:
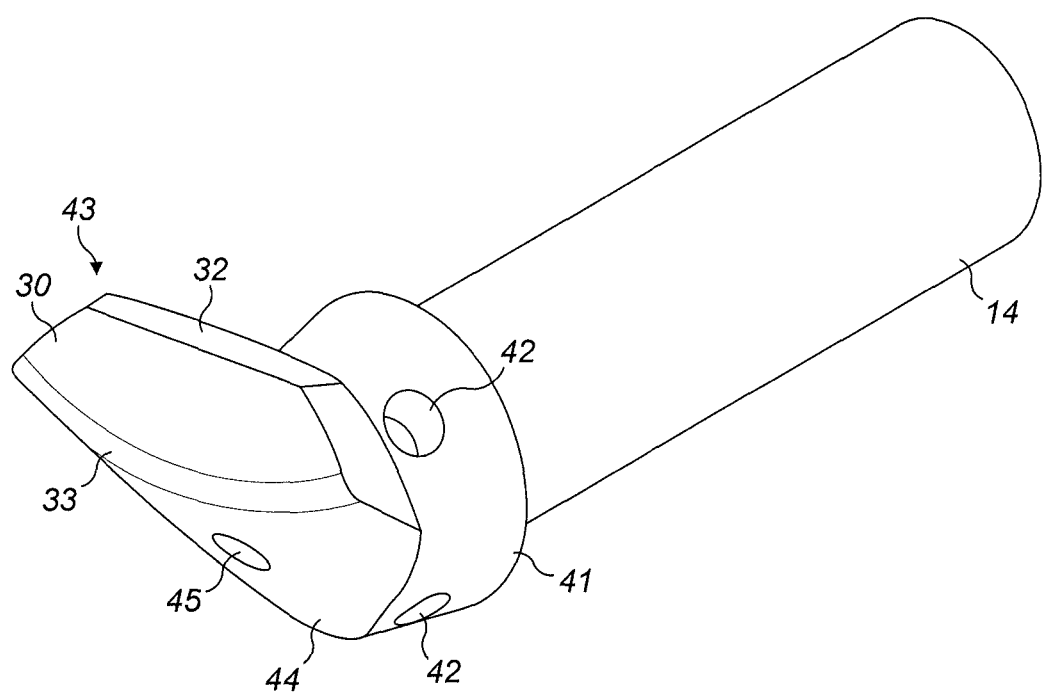
FIG. 9 is a perspective view of a part of the tip of FIG. 8.

FIGS. 8 & 9 show an alternative instrument, in which like features are designated with like reference numerals. Shaft 14, return electrode 15 and collar 18 are as previously described, but body portion 22 is now in the form of a tapered conical member 41. Suction apertures 42 are spaced around the circumference of the conical member 41. Hook portion 43 is different from the hook portion 23 of FIGS. 2 to 7, in that the hook portion 43 contains features from both the hook portion 23 and body portion 22 of the previous embodiments. Hook portion 43 includes front and back faces 30 & 31 tapering towards a top edge 32, and an end face 33 as before. However, the hook portion 43 also includes a sloping under-face 44 similar to the bottom face 27 of the previous embodiments but this time forming part of the hook member 43. Under-face 44 is provided with a suction aperture 45, in communication with the general suction lumen as previously described.

The operation of the instrument is generally as previously described, with the suction apertures 42 aspirating tissue, fluid, or other debris from the general area of the conical member 41, while the suction aperture 45 aspirates matter from the general area of the hook portion 43. The problem of providing effective suction for a sharp-edged chisel-tip electrode is thereby overcome. Again, effective suction is maintained by the provision of the plurality of suction apertures located at different positions across the outer surface of the electrode, and facing in different directions such that occlusion of all of the apertures by being pressed into tissue that is being treated is not possible; in use there should always be at least one aperture, and usually more than one, facing in an opposite direction or direction generally away from the tissue, such that it does not become occluded or otherwise blocked with tissue.

Alternative embodiments will be envisaged by those skilled in the art without departing from the scope of the present invention. For example, the electrosurgical instrument can also be used for delivering a blended power output. This is achieved by automatically alternating the output of the RF generator 1 between the coagulation and vaporisation power levels, so that more haemostasis is produced then is possible in the vaporisation mode. As a consequence, the speed of tissue debulking is reduced, but the increased haemostasis is useful when cutting or debulking vascular tissue structures. Alternatively, the output of the RF generator 1 can be pulsed at the vaporisation power level, without cycled activation of the coagulation mode. This produces a less aggressive tissue vaporisation than occurs in the vaporisation mode, with a consequent reduction in both bubble formation and the risk of tissue charring.

The invention claimed is:

1. An electrode for an electrosurgical instrument, the electrode having a longitudinal axis and comprising:
   a body portion at a first angle with respect to the longitudinal axis, the body portion increasing in width along an entirety of the body portion as the body portion extends distally along the longitudinal axis;
   a hook portion extending from the body portion at a second angle to the longitudinal axis; and
   a plurality of electrode apertures providing a suction lumen through the electrode, the plurality of electrode apertures comprising at least one hook aperture in the hook portion, and a plurality of body apertures in the body portion distributed around the body portion such that the plurality of body apertures in the body portion face different directions.

2. The electrode according to claim 1, wherein the first angle is non-zero.

3. The electrode according to claim 1, wherein the electrode also includes side faces on the body portion, the side faces facing laterally with respect to the longitudinal axis.

4. The electrode according to claim 3, wherein there is at least one of the plurality of body apertures on each of the side faces.

5. The electrode according to claim 1, wherein the electrode includes one or more end faces at a distal tip of the electrode.

6. The electrode according to claim 5, wherein the one or more end faces of the electrode are part of the hook portion.

7. The electrode according to claim 5, wherein the at least one hook aperture is provided in an end face of the one or more end faces of the electrode.

8. The electrode according to claim 1, wherein the body portion includes a prime suction lumen, and the plurality of electrode apertures are in communication with the prime suction lumen.

9. The electrode according to claim 1, wherein the plurality of body apertures are substantially equiangularly arranged around the longitudinal axis facing outwards therefrom.

10. The electrode according to claim 1, wherein the at least one hook aperture is distal facing with respect to the hook portion.

11. An electrosurgical instrument comprising an instrument shaft having a longitudinal axis, a suction lumen extending at least partially along the instrument shaft, and a chisel electrode at one end of the instrument shaft, the chisel electrode comprising:
   a body portion at a first angle with respect to the longitudinal axis, the body portion increasing in width along an entirety of the body portion as the body portion extends distally along the longitudinal axis,
   a hook portion extending from the body portion at a second angle to the longitudinal axis;
   a plurality of electrode apertures in communication with the suction lumen, the plurality of electrode apertures comprising at least one hook aperture present in the hook portion, and a plurality of body apertures present in the body portion distributed around the body portion such that the plurality of apertures in the body portion face different directions.

* * * * *